United States Patent

Kahsnitz et al.

[11] Patent Number: 5,177,229
[45] Date of Patent: Jan. 5, 1993

[54] PROCESS FOR THE PREPARATION OF ESTERS

[75] Inventors: John Kahsnitz, Haltern; Alfred Oberholz, Marl; Udo Knippenberg, Haltern; Michael Zölffel, Marl, all of Fed. Rep. of Germany

[73] Assignee: Hüls Aktiengesellschaft, Marl, Fed. Rep. of Germany

[21] Appl. No.: 727,950

[22] Filed: Jul. 10, 1991

[30] Foreign Application Priority Data

Aug. 31, 1990 [DE] Fed. Rep. of Germany ....... 4027639

[51] Int. Cl.$^5$ .............................................. C11C 3/00
[52] U.S. Cl. ..................................... 554/167; 554/162; 554/161; 560/129
[58] Field of Search ................. 260/410.9 R; 550/167, 550/161, 162; 560/129

[56] References Cited

U.S. PATENT DOCUMENTS 5,008,046 4/1991 Bremus et al. .................... 260/410.6

FOREIGN PATENT DOCUMENTS

| 3121383 | 2/1992 | Fed. Rep. of Germany . |
| WO9008127 | 7/1990 | PCT Int'l Appl. . |
| WO9101966 | 2/1991 | PCT Int'l Appl. . |
| 1387704 | 3/1975 | United Kingdom . |

OTHER PUBLICATIONS

Chem. Ing. Tech. 54 (1982) p. 163, Schoenmakers et al, and English Trans.
Chemie. Ingenieur. Technik., bd. 54, nr. 2, 1982, H. Schoenmakers (Filed Feb. 24, 1992).

*Primary Examiner*—Jose G. Dees
*Assistant Examiner*—D. D. Carr
*Attorney, Agent, or Firm*—Oblon, Spivak, McClelland, Maier & Neustadt

[57] ABSTRACT

Alcohols and acids are esterified by means of liquid-phase equilibrium reactions on ion exchangers in an apparatus comprising a prereactor and a rectifying column with external reactors. The process is characterized by the fact that a portion of one of the starting compounds is fed directly to the external reactors.

12 Claims, 1 Drawing Sheet

PROCESS FOR THE PREPARATION OF ESTERS

BACKGROUND OF THE INVENTION

1. Field of the Invention

The present invention relates to a process for the preparation of esters from alcohols and acids by means of liquid-phase equilibrium reactions on ion exchangers, which process is carried out in a prereactor and in a rectifying column with external reactors.

2. Discussion of the Background

Since esterification is not a very one-sided equilibrium reaction, special measures, as for example, the addition of excess starting compound or a multi-step reaction, are taken in order to increase the conversion of valuable feedstocks and to obtain the esters in maximum yield and purity.

Thus, esterification on cation exchangers is carried out, according to DE-C-1,768,104 in a precolumn and a subsequent reaction distillation column.

Due to the high thermal load of ion exchangers in a reaction distillation column and due to the difficult separation by means of distillation in the presence of ion exchangers, esterification and rectification are spacially separated in other processes. In DE-C-3,121,383, esterification is carried out in a reactor on a cation exchanger. In a subsequent cation exchanger-free distillation column, the reaction mixture is separated. By recycling unconverted starting compounds into the reactor, high yields of ester can be obtained.

H. Schoenmakers and W. Bühler, *Chem.-Ing.-Tech.*, Vol. 54, p. 153 (1982), disclose another possibility of esterification. They use an apparatus, which comprises a prereactor and a distillation column with external reactors. The esterification is catalyzed by ion exchangers in the reactors. Thus, the alcohol-acid mixture is guided first into the prereactor. The reaction mixture is fed into the distillation column. The liquid phase draining into the column is led out multiple times on the side, directed through an external reactor and returned from there to the next lower plate of the column.

With equimolar quantities of alcohol and acid or with a slight excess of alcohol quantities, conversions ranging from about 55 to 60% are obtained. Naturally, the process avoids recycling unconverted starting compounds into the prereactor, but the conversions for commercial use are very low.

SUMMARY OF THE INVENTION

Accordingly, one object of the present invention is to provide a method for preparing esters in improved conversion and yield.

It is another object of the invention to provide a method to improve the conversion and yield during esterification in a prereactor and a rectifying column with external reactors, where the liquid phase on a plate of the column is withdrawn from the side, is directed to an external reactor, and from there returned to the next lower plate of the column.

These and other objects, which will become apparent during the following detailed description, have been achieved by the inventor's discovery that the conversion and yield during esterification, in a prereactor and a rectifying column with external reactors, where the liquid phase on a plate of the column is withdrawn from the side, is directed to an external reactor, and from there returned to the next lower plate of the column, are improved when a starting compound is also fed directly to the external reactors.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
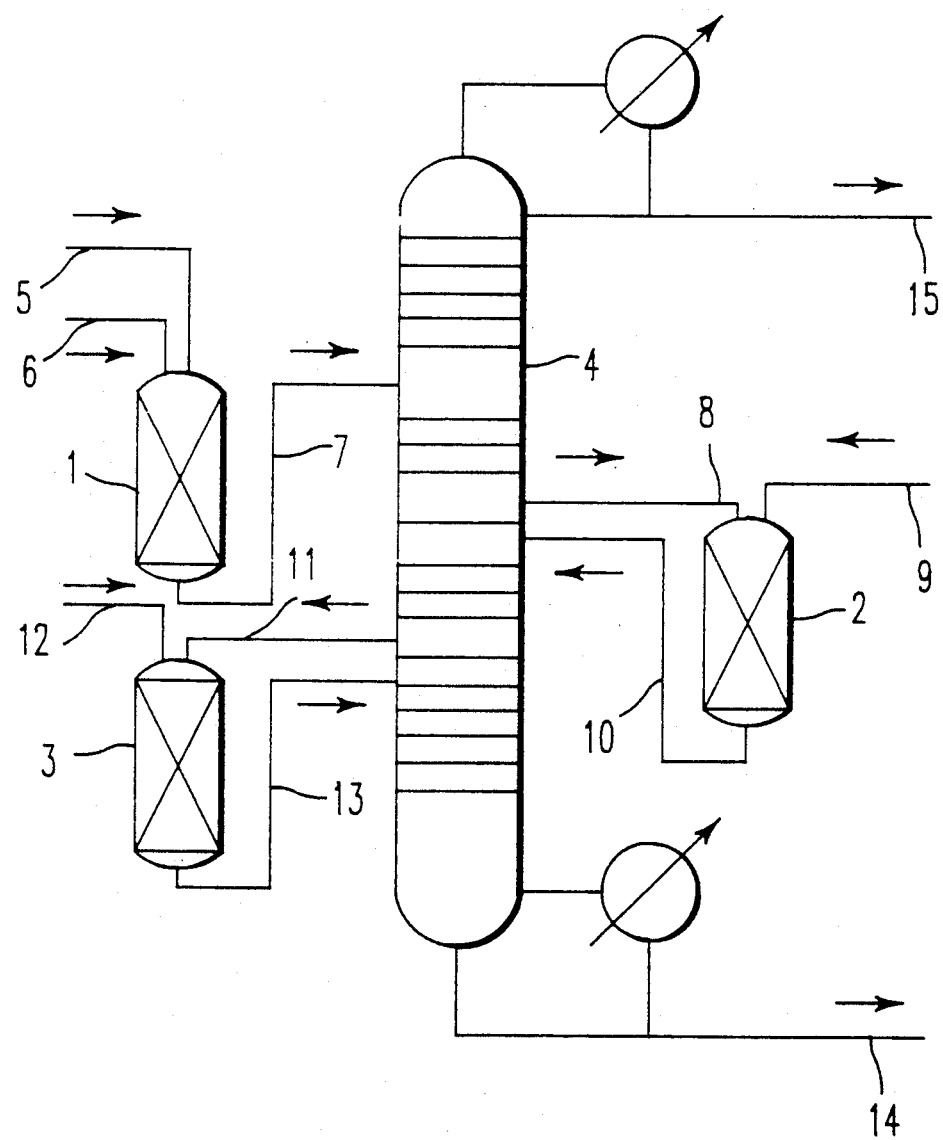
FIG. 1 illustrates schematically an apparatus for carrying out the present method.

Starting compounds in the sense of the present invention are alcohols and acids. They are preferably added in such quantities to the prereactor such that 0.2 to 6 equivalents, preferably 1 to 5 equivalents, of alcohol per one equivalent of acid are added. In so doing, a lesser quantity of the more valuable component is usually added.

The present invention requires no specific acids and alcohols. Preferably, however, long chain carboxylic acids having 6 to 20 carbon atoms and alcohols having 1 to 6 carbon atoms are used.

Suitable carboxylic acids are, for example, hexanoic decanoic, dodecanoic and tetradecanoic acid, palmitic, linoleic and stearic acid, and benzoic acid. Also polyvalent acids such as adipic acid, dodecanedioic acid, citric acid or isophthalic acid can be added. In particular, aliphatic monocarboxylic acids having 10 to 16 carbon atoms are preferably added.

Suitable alcohols are, for example, methanol, ethanol, propanol, isopropanol, butanol, pentanol, hexanol, and cyclohexanol. In particular, methanol and ethanol are preferably added.

In a special embodiment of the present invention, 1 to 5 equivalents of alcohol per 1 equivalent of acid are added to the prereactor.

Commercially available acidic cation exchangers may be used as the ion exchangers. Suitable cationic exchangers include acrylic or methacrylic acid which has been crosslinked with a difunctional monomer, e.g., divinylbenzene and sulfonated copolymers of styrene and divinylbenzene. Specific examples of such cationic exchangers are found in Gordon et al, *The Chemist's Companion: A Handbook of Practical Data, Techniques, and References*, Wiley, N.Y., p. 386 (1972), which is incorporated herein by reference.

Preferably, rectifying columns having 5 to 30 theoretical plates are used. Preferably, 2 to 5 external reactors are attached to one rectifying column.

Preferably, the entire liquid phase flowing down is fed into the external reactors. If only one part of the liquid phase is drained off into the external reactors, a lower conversion is obtained.

The starting compound, which is metered into the external reactors, is preferably the compound of which an equivalent or excess quantity was added to the prereactor. Since the acid in the present process is preferably the more valuable compound, and therefore, an equivalent or lesser quantity is usually added, alcohol is preferably added to the external reactors.

In an especially preferred embodiment 0.2 to 5 equivalents, more preferably 1 to 3 equivalents, of alcohol per equivalent of acid added to the prereactor are added to each external reactor.

It is especially advantageous to evaporate in part the mixture leaving the external reactors. Preferably up to 85 mole % of the mixture is thereby evaporated.

As before, the remaining liquid phase is then recycled to the first plate below the discharge point. The vapor phase is, however, led separately into the column, and in particular to the first plate above the discharge point.

A partial evaporation occurs primarily when the reactors are under a higher pressure than the column. Partial evaporation can occur, for example, with the aid of a flash evaporator. In a very preferred method 40 to 80 mole % of the mixture is evaporated.

Due to the limited thermal stability of the acidic ion exchangers, esterification in the prereactor and in the external reactors is conducted at temperatures up to about 120° C. In so doing temperatures ranging from 40° to 100° C. are preferably used.

In the rectifying column, the reaction products are separated preferably at normal pressure. However, pressures of up to about 0.8 MPa can also be applied.

It can be an advantage if the pressure in the reactor is higher than in the column. Generally, the pressure in the reactors ranges from normal pressure to about 1 MPa.

According to the process of the present invention, the conversion of the insufficient compound is increased. The yield of esters is clearly improved, and esters with reduced acid number are prepared.

FIG. 1 shows schematically an apparatus comprising a prereactor 1 and a rectifying column 4 with external reactors 2 and 3. During a conversion in which alcohol is metered into the external reactors and in which no partial evaporation is performed, the procedure is as follows.

The acid is led into prereactor 1 via line 5, the alcohol via line 6. The reaction product flows via line 7 into column 4. The liquid phase is directed via line 8 into the reactor 2; alcohol is metered through line 9. The reaction product is recycled through line 10. The liquid phase is led out again via line 11. Alcohol is directed through line 12. From reactor 3 the product recycles into the column through line 13. Esters and residual acid are led out through line 14. Distillate, alcohol and water are drained off via line 15.

Other features of the invention will become apparent in the course of the following descriptions of exemplary embodiments which are given for illustration of the invention and are not intended to be limiting thereof.

EXAMPLES

In Examples 1 to 3 and in Comparative Example A, a heated rectifying column driven at normal pressure and having an internal diameter of $d_i = 80$ mm and having 18 physical plates is used according to FIG. 1. The three reactors are identical and contain a total of 2.9 kg of acidic ion exchanger (Lewatit ® SPC 108, Bayer AG, D-5090 Leverkusen). At the head of the column the temperature is 70° C., in the boiler 150° C. The temperature of the reactors is

| | |
|---|---|
| $T_{prereactor}$ = | 66.0° C. |
| $T_{external\ reactor\ 2}$ = | 55.0° C. |
| $T_{external\ reactor\ 3}$ = | 63.5° C. |

Comparative Example A (According to H. Schoenmakers)

6.03 mol/h of dodecanoic acid and 18.24 mol/h of methanol are introduced into prereactor 1. Liquid phase exclusively withdrawn from the column is fed to both external reactors. No more methanol is added.

| | |
|---|---|
| Total conversion: | 70.3%. based on dodecanoic acid |
| Total energy consumption: | 311 W |

Example 1

6.03 mol/h of dodecanoic acid and 6.03 mol/h of methanol are introduced into prereactor 1. In addition to withdrawn liquid phase, methanol is also fed to both external reactors: 6.42 mol/h of methanol for external reactor 2 and 5.39 mol/h of methanol for external reactor 3.

| | |
|---|---|
| Total conversion: | 82.8%. based on dodecanoic acid |
| Total energy consumption: | 305 W |

Comparative Example A and Example 1 show that under the same reaction conditions with equal quantities of acid and almost equal total quantity of alcohol and with comparable energy consumption, a conversion that is higher by 12.5% is obtained according to the process of the present invention.

Example 2

4.14 mol/h of dodecanoic acid and 12.34 mol/h of methanol are introduced into prereactor 1. In addition to withdrawn liquid phase, methanol is also fed to both external reactors: 12.65 mol/h of methanol for external reactor 2 and 12.96 mol/h of methanol for external reactor 3.

| | |
|---|---|
| Total conversion: | 99.5%, based on dodecanoic acid |
| Total energy consumption: | 425 W |

Example 3

6.03 mol/h of dodecanoic acid and 17.98 mol/h of methanol are introduced into prereactor 1. In addition to withdrawn liquid phase, methanol is also fed to both external reactors: 17.98 mol/h of methanol for external reactor 2 and 17.98 mol/h of methanol for external reactor 3. However, deviating from the aforementioned examples, the external reactor 2 is driven at 0.5 MPa and 100° C. The product of the external reactor 2 is expanded in a subsequent flash evaporator. 10.5 mol/h of liquid phase are fed to the first plate below the discharge point. 32.3 mol/h of the vapor phase are directed separately to the first plate over the discharge point of the column.

| | |
|---|---|
| Total conversion: | 99.7%, based on dodecanoic acid |
| Total energy consumption: | 300 W + compression work before external reactor 2. |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for the preparation of an ester, comprising reacting an alcohol and an acid by means of a liquid-phase equilibrium reaction on an ion exchanger in a prereactor to obtain reaction products, and separating said reaction products in a rectifying column with one or more external reactors, wherein the liquid phase on a plate of said rectifying column is withdrawn, is directed to an external reactor and then returned to the next lower plate of said rectifying column, wherein an additional amount of said alcohol or said acid is also fed directly to at least one of said external reactors.

2. The process of claim 1, wherein 0.2 to 6 equivalents of said alcohol per one equivalent of said acid are introduced to said prereactor.

3. The process, of claim 1, wherein 1 to 5 equivalents of said alcohol per 1 equivalent of said acid are added to said prereactor and wherein 0.2 to 5 equivalents of said alcohol per equivalent of said acid added to said pre-reactor are added to each of said external reactors.

4. The process, of claim 1, wherein said acid is a carboxylic acid having 6 to 20 carbon atoms and said alcohol has 1 to 6 carbon atoms.

5. The process, of claim 4, wherein said carboxylic acid has 10 to 16 carbon atoms and said alcohol is methanol or ethanol.

6. The process, of claim 1, wherein the reaction mixture leaving said external reactors is partially vaporized to obtain a remaining liquid phase and a vapor phase and said remaining liquid phase is recycled to the next lower plate and said vapor phase is recycled to the next higher plate of the column, based on the plate from which the reaction products were removed from said rectifying column.

7. The process, of claim 6, wherein up to 85 mole % of the reaction mixture is vaporized.

8. The process, of claim 1, wherein said rectifying column has 2 to 5 external reactors.

9. The process of claim 1, wherein said alcohol is fed directly to said external reactors.

10. The process of claim 2, wherein 1 to 3 equivalents of alcohol per 1 equivalent of acid added to the pre-reactor are added to each external reactor.

11. The process of claim 1, wherein said reaction of said alcohol and said acid in said pre-reactor is effected at a temperature of up to 120° C.

12. The process of claim 11, wherein said reaction of said alcohol and said acid in said pre-reactor is effected at a temperature of from about 40° to 100° C.

* * * * *